(12) United States Patent
Fleming et al.

(10) Patent No.: US 6,787,302 B2
(45) Date of Patent: Sep. 7, 2004

(54) METHOD AND APPARATUS FOR PROKARYOTIC AND EUKARYOTIC CELL QUANTITATION

(75) Inventors: James E. Fleming, Spokane, WA (US); Jason Buck Somes, Spokane, WA (US)

(73) Assignee: GenPrime, Inc., Spokane, WA (US)

(*) Notice: Subject to any disclaimer, the term of this patent is extended or adjusted under 35 U.S.C. 154(b) by 229 days.

(21) Appl. No.: 10/087,200

(22) Filed: Mar. 1, 2002

(65) Prior Publication Data

US 2002/0168630 A1 Nov. 14, 2002

Related U.S. Application Data

(63) Continuation-in-part of application No. 09/696,710, filed on Oct. 24, 2000, now Pat. No. 6,673,568.
(60) Provisional application No. 60/163,738, filed on Oct. 25, 1999.

(51) Int. Cl.$^7$ ............................. C12Q 1/00; C12Q 1/37; C12Q 1/02; C12Q 1/04; G01N 33/53
(52) U.S. Cl. .............................. 435/4; 435/24; 435/23; 435/975; 435/34; 435/29
(58) Field of Search ............................... 435/4, 24, 23, 435/975, 34, 29

(56) References Cited

U.S. PATENT DOCUMENTS

| | | | |
|---|---|---|---|
| 4,190,328 A | 2/1980 | Levine et al. ............... 350/320 |
| 4,242,447 A | 12/1980 | Findl et al. ..................... 435/39 |
| 4,288,539 A | 9/1981 | McAleer et al. ............... 435/7 |
| 4,544,546 A | 10/1985 | Wang et al. .................. 424/7.1 |
| 4,710,472 A | 12/1987 | Saur et al. ................... 435/287 |
| 4,859,584 A | 8/1989 | Horan et al. .................. 435/29 |
| 5,057,413 A | 10/1991 | Terstappen et al. ............. 435/6 |
| 5,314,805 A | 5/1994 | Haugland et al. ............. 435/29 |
| 5,436,134 A | 7/1995 | Haugland et al. ............. 435/34 |
| 5,437,980 A | 8/1995 | Haugland ....................... 435/6 |
| 5,496,700 A | * 3/1996 | Ligler et al. .................. 435/7.1 |
| 5,534,416 A | 7/1996 | Millard et al. ................ 436/34 |
| 5,545,535 A | 8/1996 | Roth et al. ..................... 435/34 |
| 5,563,070 A | 10/1996 | Yamamoto et al. ........... 436/63 |
| 5,582,984 A | 12/1996 | Bieniarz et al. ................ 435/6 |
| 5,658,751 A | 8/1997 | Yue et al. ...................... 435/34 |
| 5,695,946 A | 12/1997 | Benjamin et al. .......... 435/7.32 |
| 5,701,012 A | * 12/1997 | Ho ........................... 250/461.2 |
| 5,734,058 A | 3/1998 | Lee ............................. 546/176 |
| 5,798,115 A | 8/1998 | Santerre et al. ............. 424/423 |
| 5,804,448 A | 9/1998 | Wang et al. ................... 436/63 |
| 5,888,736 A | 3/1999 | Lacroix et al. ................. 435/6 |
| 5,895,922 A | * 4/1999 | Ho ........................... 250/491.2 |
| 5,939,282 A | 8/1999 | Harman et al. ............... 435/29 |
| 5,968,762 A | 10/1999 | Jadamec et al. .............. 435/18 |
| 5,994,067 A | 11/1999 | Wood et al. .................... 435/6 |

FOREIGN PATENT DOCUMENTS

| | | |
|---|---|---|
| DE | 19832007 A1 | 1/2000 |
| GB | 1503828 | 3/1978 |
| WO | WO 97/17463 | 5/1997 |

OTHER PUBLICATIONS

Ahn et al., "PicoGreen quantitation of DNA:effective evaluation of samples pre- or post- PCR," *Nucleic Acids Research* 24(13):2623–2625, 1996.

Blaheta et al., "Development of an ultrasensitive in vitro assay to monitor growth of primary cell cultures with reduced mitotic activity," *Journal of Immunological Methods* 211:159–169, 1998.

(List continued on next page.)

*Primary Examiner*—Louise N. Leary
(74) *Attorney, Agent, or Firm*—Seed Intellectual Property Law Group PLLC (57) ABSTRACT

This invention describes methods and kits for detecting and quantifying viable cells in a sample using fluorescent dyes that can be internalized predominantly by viable cells and have fluorescent properties measurably altered when bound to target components. These methods and kits provide a rapid and cost-effective means of detecting potential biological threats in the field.

22 Claims, 3 Drawing Sheets

TBAK Correlation Chart for Redi-Set
Mesophilic Bacteria

| TBAK Reading | Colony Forming Units/ml |
|---|---|
| 15000 | $6.0 \times 10^8$ |
| 13500 | $5.4 \times 10^8$ |
| 12000 | $4.8 \times 10^8$ |
| 10000 | $4.2 \times 10^8$ |
| 8500 | $3.6 \times 10^8$ |
| 7000 | $3.0 \times 10^8$ |
| 5500 | $2.4 \times 10^8$ |
| 3500 | $1.8 \times 10^8$ |
| 2000 | $1.2 \times 10^8$ |

OTHER PUBLICATIONS

Bolger et al., "Fluorescent Dye Assay for Detection of DNA in Recombinant Protein Products," *BioTechniques* 23(3):532–536, 1997.

Catt et al., "Hoechst staining and exposure to UV laser during flow cytometric sorting does not affect the frequency of detected endogenous DNA nicks in abnormal and normal human spermatozoa," *Molecular Human Reproduction* 821–825, 1997.

Chadwick et al., "Heterozygote and Mutation Detection by Direct Automated Fluorescent DNA Sequencing Using a Mutant Taq DNA Polymerase," *BioTechniques* 20(4):676–683, Apr. 1996.

Emaus et al., "Rhodamine 123 as a probe of transmembrane potential in isolated rat–liver mitochondria: spectral and metabolic properties," *Biochimica et Biophysica Acta* 850:436–448, 1986.

Enger, Ø., "Use of the Fluorescent Dye PicoGreen™ for Quantification of PCR Products after Agarose Gel Electrophoresis," *BioTechniques* 21(3):372–374, Sep. 1996.

Ferguson and Denny, "Microbial mutagenic effects of the DNA minor groove binder pibenzimol (Hoechst 33258) and a series of mustard analogues," *Mutation Research* 329(1):19–27, 1995.

Ferrari et al., "Analytical Methods for the Characterization of Cationic Lipid–Nucleic Acid Complexes," *Human Gene Therapy* 9:341–351, Feb. 10, 1998.

Griffith et al., "An evaluation of luminometry as a technique in food microbiology and a comparison of six commercially available luminometers," *Food Science and Technology Today* 8(4):209–216, 1994.

Hall et al., "An Approach to High–throughput Genotyping," *Genome Research* 6:781–790, 1996.

Haugland, R.P., *Handbook of Fluorescent Probes and Research Chemicals*, Spence, M. (ed.), Molecular Probes, Eugene, OR, 1996, "PicoGreen dsDNA Quantitation Reagent," p. 162.

Holst et al., "Allosteric modulation of AMPA–type glutamate receptors increases activity of the promoter for the neural cell adhesion molecule, N–CAM," *Proc. Natl. Acad. Sci. USA* 95:2597–2605, Mar. 1998.

Hopwood et al., "Rapid Quantification of DNA Samples Extracted from Buccal Scrapes Prior to DNA Profiling," *BioTechniques* 23:18–20, Jul. 1997.

Latt and Wohlleb, "Optical Studies of the Interaction of 33258 Hoechst with DNA, Chromatin, and Metaphase Chromosomes," *Chromosoma* 52(4):297–316, 1975.

Mansfield et al., "Nucleic acid detection using non–radioactive labeling methods," *Molecular and Cellular Probes* 9:145–156, 1995.

Marie et al., "Application of the Novel Nucleic Acid Dyes YOYO–1, YO–PRO–1, and PicoGreen for Flow Cytometric Analysis of Marine Prokaryotes," *Applied and Environmental Microbiology* 62(5):1649–1655, May 1996.

Matsuzaki et al., "Nuclear Staining for Laser Confocal Microscopy," *Acta Histochem. Cytochem.* 30(3):309–314, 1997.

Moran et al., "Nonelectrophoretic Genotyping Using Allele–Specific PCR and a dsDNA–Specific Dye," *BioTechniques* 24:206–212, Feb. 1998.

Murakami et al., "Quantitation of Adenovirus DNA and Virus Particles with the PicoGreen Fluorescent Dye," *Analytical Biochemistry* 274:283–288, 1999.

Nebe–von Caron et al., "Assessment of bacterial viability status by flow cytometry and single cell sorting," *Journal of Applied Microbiology* 84:988–998, 1998.

Niemeyer et al., "Fluorometric Polymerase Chain Reaction (PCR) Enzyme–Linked Immunosorbent Assay for Quantification of Immuno–PCR Products in Microplates," *Analytical Biochemistry* 246:140–145, 1997.

Papadimitriou and Lelkes, "Measurement of cell numbers in microtiter culture plates using the fluorescent dye Hoechst 33258," *Journal of Immunological Methods* 162:41–45, 1993.

Parpais et al., "Effect of phosphorus starvation on the cell cycle of the photosynthetic prokaryote *Prochlorococcus* spp.," *Marine Ecology Progress Series* 32:265–274, Feb. 29, 1996.

Pinder et al., *New Techniques in Food and Beverage Microbiology*, Kroll et al. (eds.), Blackwell Scientific Publications, 1993, chapter 6, "Detection and Enumeration of Viable Bacteria by Flow Cytometry," pp. 67–86.

Rago et al., "DNA Fluorometric Assay in 96–Well Tissue Culture Plates Using Hoechst 33258 after Cell Lysis by Freezing in Distilled Water," *Analytical Biochemistry* 191:31–34, 1990.

Romppanen et al., "Optimal Use of the Fluorescent PicoGreen Dye for Quantitative Analysis of Amplified Polymerase Chain Reaction Products on Microplate," *Analytical Biochemistry* 279:111–114, Mar. 2000.

Rundquist et al., "Cytofluorometric Quantitation of Acridine Orange Uptake by Cultured Cells," *Acta Pathologica Microbiol. Immunol. Scand. Sect. A* 92:303–309, 1984.

Seville et al., "Fluorometric Assay for DNA Polymerase and Reverse Transcriptase," *BioTechniques* 21(4):664–672, Oct. 1996.

Singer et al., "Characterization of PicoGreen Reagent and Development of a Fluorescence–Based Solution Assay for Double–Stranded DNA Quantitation," *Analytical Biochemistry* 249:228–238, 1997.

Singer et al., *Biotechnology International*, Connor and Fox (eds.), Universal Medical Press, Inc., 1997, "Sensitive Fluorescent Stains for Detecting Nucleic Acids in Gels and Solutions," pp. 267–277.

Singhal et al., "DNA–Protein Interactions and Separation of Restriction Fragments by Capillary Electrophoresis," *The FASEB Journal* 9(6):A1423, Abstract No. 965, Apr. 24, 1995.

Suzuki et al., "Fluorescence Counter–Staining of Cell Nuclear DNA for Multi–Color Laser Confocal Microscopy," *Acta. Histochem. Cytochem.* 31(4):297–301, 1998.

Tranvik, L.J., "Rapid fluorometric assay of bacterial density in lake water and seawater," *Limnol. Oceanogr.* 42(7):1629–1634, 1997.

Veldhuis et al., "Cellular DNA Content of Marine Phytoplankton Using Two New Fluorochromes: Taxonomic and Ecological Implications," *J. Phycol.* 33:527–541, 1997.

Yan et al., "Characteristics of Different Nucleic Acid Staining Dyes for DNA Fragment Sizing by Flow Cytometry," *Anal. Chem.* 71(24):5470–5480, Dec. 15, 1999.

Zhu et al., "Cell cycle–dependent modulation of telomerase activity in tumor cells," *Proc. Natl. Acad. Sci. USA* 93:6091–6095, Jun. 1996.

\* cited by examiner

TBAK Correlation Chart for Redi-Set

Mesophilic Bacteria

| TBAK Reading | Colony Forming Units/ml |
|---|---|
| 15000 | $6.0 \times 10^8$ |
| 13500 | $5.4 \times 10^8$ |
| 12000 | $4.8 \times 10^8$ |
| 10000 | $4.2 \times 10^8$ |
| 8500 | $3.6 \times 10^8$ |
| 7000 | $3.0 \times 10^8$ |
| 5500 | $2.4 \times 10^8$ |
| 3500 | $1.8 \times 10^8$ |
| 2000 | $1.2 \times 10^8$ |

METHOD AND APPARATUS FOR PROKARYOTIC AND EUKARYOTIC CELL QUANTITATION

CROSS-REFERENCES TO RELATED APPLICATIONS

This application is a continuation-in-part of U.S. patent application Ser. No. 09/696,710, filed on Oct. 24, 2000, now U.S. Pat. No. 6,673,568, which claims priority to U.S. Provisional Application No. 60/163,738, filed on Oct. 25, 1999, all of which are incorporated herein by reference in their entirety.

TECHNICAL FIELD

The present invention relates generally to methods for the rapid detection of viable cells involving staining viable cells in a sample with a fluorescent dye and measuring the fluorescence. The invention is more particularly related to methods and kits for the rapid identification of microbes in an environmental sample.

BACKGROUND OF THE INVENTION

Biowarfare and bioterrorism include the intentional or the alleged use of viruses, bacteria, fungi and toxins to produce death or disease in humans, animals or plants. While biowarfare poses substantial health risks, bioterrorism also possesses the ability to severely disrupt individuals' lives, as well as societies and economies. Unfortunately, hoaxes and false alarms similarly disrupt lives and work. Individuals affected by both credible and false biowarfare threats are often forced to wait long time periods while officials determine if a credible biological threat exists, even though only one or two out of several hundred responses may result in a credible threat. Clearly, methods of rapidly determining whether a credible biological threat exists are vitally important in preventing both disease and societal and economic disruption.

A variety of methods are currently employed for the detection of microbial biowarfare agents, such as bacteria and yeast. These methods include, but are not limited to, conventional cell viability assays such as the standard plate count, dye reduction and exclusion methods, electrometric techniques, microscopy, flow cytometry, bioluminescence, colorimetry, and turbidity. However, such methods are generally not useful for rapid detection, as required for field testing and rapid determination of the existence of a potential biological threat. These methods typically require highly trained personnel and expensive instrumentation. In addition, many of these assays require substantially pure populations of cells or long incubation periods.

Additional methods specifically designed to detect biological threats include, for example, immunodiagnostic assays, DNA assays using real-time polymerase chain reaction (PCR), mass spectrometry, enhanced bioluminescence assays, protein nanoarrays, volatile organic compound analysis, and multi photon detection. Again, most of these assays require expensive instrumentation and highly-trained personnel, and cannot be rapidly performed in the field.

Several handheld kits for the detection of biowarfare agents have been described. Sensitive Membrane Antigen Rapid Test (SMART™) Tickets are currently sold commercially for the rapid detection of *Bacillus anthracis* spores, *V. cholerae* serotype 01, *Yersina pestis*, and *Botulism toxin*. SMART™ Tickets employ a calorimetric immunoassay designed for the direct presumptive recognition or detection of a presumed biowarfare agent(s). However, the analytical sensitivity of these assays is limited by the current technology, and data provided by manufacturers indicate that a minimum of 10,000 spores is required to generate a positive signal. This number of spores would require a relatively heavy contamination of the area (sample) being tested.

Bio Threat Alert™ test strips are currently marketed for the detection of *Bacillus anthracis*, ricin toxin, Botulinum Toxin, Staphococcal Enterotoxin B, *Yersina pestis*, and *Francisella tularensis*. The Bio Threat Alert™ test strip employs agent-specific antibodies to positively identify the potential threat. Screening results are produced in approximately 15 minutes and may be read visually or using the Guardian Bio Threat Alert™ Test Strip Reader.

Although SMART™ Tickets and Bio Threat Alert test strips are designed for rapid field detection of biowarfare agents, their usefulness appears limited by low sensitivity of detection and their ability to detect a very limited number of microbial biowarfare agents. Further, such antibody-dependent tests are susceptible to the possibility of designed or naturally occurring biological mechanisms that would result in an escape from immune detection. For example, several standard dual or multidye fluorescence filter set are known and available from microscope and filter manufacturers including Zeiss, Leica, Chroma Technologies, Nikon and the like.

The present invention for the detection and quantitation of cells is designed to overcome problems that have been identified within the field. The present technology circumvents the need for training personnel in how to plate, grow and count viable cells from colonies on agar plates and eliminates nearly all training and maintenance costs associated with most other microbial biowarfare agent detection and quantification methods. In addition, the invention substantially decreases the time needed for biowarfare agent detection, permitting more accurate detection in less than twenty minutes, while still allowing for the detection and quantification of any live cell present in the test sample. Finally, the technology offers substantial cost savings over most existing methods of microbial biowarfare agent detection and quantitation.

BRIEF SUMMARY OF THE INVENTION

Briefly, the present invention describes methods and kits for detecting and quantifying viable cells in a sample using fluorescent dyes that can be actively internalized by viable cells and have fluorescence properties measurably altered when bound to target components.

In one embodiment of the present invention, a method for quantifying viable cells in a sample is disclosed, comprising the following steps: (1) contacting a sample with a fluorescent dye, wherein the dye is actively or passively internalized by the cells and has fluorescence properties that are measurably altered when bound to target components; (2) detecting total fluorescence of the sample; and (3) comparing the fluorescence produced by the sample to the fluorescence produced by a control substance. Within certain embodiments, (1) the cells in the sample are bacteria, spores, and yeast and other fungi; (2) the fluorescent dye binds to DNA of the viable cells; (3) the sample is treated with DNase before it is mixed with the fluorescent dye; (4) the sample is treated with an agent that affects a cell membrane property of the cells (e.g., a detergent) prior to, subsequently or concurrently with the fluorescent dye; or (5) the fluorescent dye is acridine orange, Hoechst 33258, PicoGreen™, SYTO® 16, SYBR® Green I, Texas Red®, Redmond Red™, Bodipy® Dyes, or Oregon Green™.

In certain embodiments, the cells in the sample are *Bacillus anthracis, Bacillus cereus, Clostridium botulinum, Yersinia pestis, Yersinia enterocolitica, Francisella tularensis*, Brucella species, *Clostridium perfringens, Burkholderia mallei, Burkholderia pseudomallei*, Staphylococcus species, Tuberculosis species, *Escherichia coli*, Group A Streptococcus, Group B streptococcus, *Streptococcus pneumoniae, Helicobacter pylori, Francisella tularensis, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsii, Rickettsia akari, Rickettsia prowazekii, Rickettsia canada, Coxiella burnetti, Aspergillus varieties, Mucor pusillus, Rhizopus nigricans, Candida albicans, C. parapsilosis, C. tropicalis, C. pseudotropicalis, Torulopsis glabrata, Aspergillus niger, Candida dubliniensis, Blastomyces dermatitidis, Coccidioides immitis, Histoplasma capsulatum*, Aspergillus species, Candida species, *Cryptococcus neoformans, Bacillus subtilis, Bacillus subtilus niger, Bacillus thuringiensis*, all Bacillus sp. and/or *Sporothrix schenckii.*

The present invention also discloses kits for detecting or quantifying viable cells. One such kit comprises a cell suspension solution, a fluorescent dye that can be actively internalized by viable cells, and instruction for detecting dye binding to cellular components of viable cells. The cell suspension solution may include a DNase or an agent that affects cell membrane property, such as a detergent. In certain embodiments, the fluorescent dye may be acridine orange, Hoechst 33258, PicoGreen™, SYTO® 16, SYBR® Green I, Texas Red®, Redmond Red™, Bodipy® Dyes, or Oregon Green™. Such fluorescent dyes are readily available from commercial sources including Molecular Probes (Eugene, Oreg.), Sigma Chemical (St Louis, Mo.), Amersham (Arlington Heights, Ill.), Callbiochem-Novabiochem (La Jolla, Calif.), Synthetic Genetics (San Diego, Calif.), and the like.

In another embodiment, a kit comprises a first container containing a first solution, means for placement of a sample containing an unknown number of viable cells into a solution containing a fluorescent dye that can be internalized predominately by the viable cells and binds selectively to double-stranded DNA or other specific cellular components, whereupon its fluorescence is altered to a measurable degree, and means for illuminating the mixture of first solution with said sample with excitation light and measuring fluorescence emitted by said mixture, thereby detecting the presence of viable cells in said sample.

In yet another embodiment, a kit comprises a first container containing a first solution, means for placement of a sample containing an unknown number of viable cells into a first solution, means for concentrating the solids and cells from the mixture of said first solution with said sample and retaining said solids from the remainder of said mixture, a second solution containing a fluorescent dye that can be internalized predominately by the viable cells and binds selectively to double-stranded DNA or other specific cellular components, whereupon its fluorescence is altered to a measurable degree, means for mixing said second solution with said solids to form a second mixture, and means for illuminating the mixture of said second solution with said solids with excitation light and measuring fluorescence emitted by said mixture, thereby detecting viable cells in said sample.

Upon binding, the fluorescence properties of the fluorescent dye are altered to a measurable degree. The first solution may contain a DNase or an agent that affects a bacterial cell membrane property, such as a detergent. Within certain embodiments, the fluorescent dye may be acridine orange, Hoechst 33258, PicoGreen™, SYTO® 16, SYBR® Green I, Texas Red®, Redmond Red™, Bodipy® Dyes, or Oregon Green™.

BRIEF DESCRIPTION OF DRAWINGS

FIG. 1 is a correlation of relative intensities of the fluorescent emission (TBAK readings) to the standard plate counts (colony forming units/ml) of Mesophilic Bacteria.

FIG. 2 is a chart that correlates relative fluorescence readings with colony forming units/ml of Mesophilic Bacteria.

FIG. 3 is a graph depicting the relationship of fluorescence to spore concentration using a nucleic acid binding dye such as SYTO® 16.

FIG. 4 is a bar graph depicting relative light units of common substances and comparison of the same to several microbes.

DETAILED DESCRIPTION OF THE INVENTION

As noted above, the subject invention is concerned with methods and kits for detecting and quantitating viable cells in a sample. The invention is applicable to the detection and quantitation of all types of viable cells, including eukaryotes, such as plant and animal cells (e.g., mammalian cells, particularly human cells), and prokaryotes, particularly bacteria (including both Gram-positive and Gram-negative bacteria), bacterial spores, yeast, and other fungi. Viable cells are cells that have intact cell membranes and are actually or potentially metabolically active. As used herein, spores and cysts are examples of viable cells.

In certain embodiments, the methods and kits of the invention are used to detect or quantitate biowarfare agents, including infectious agents such as bacteria and fungi, for example. Examples of bacteria and spores that may be detected according to the present invention include, but are not limited to, *Bacillus anthracis, Bacillus cereus, Clostridium botulinum, Yersinia pestis, Yersinia enterocolitica, Francisella tularensis*, Brucella species, *Clostridium perfringens, Burkholderia mallei, Burkholderia pseudomallei*, Staphylococcus species, Tuberculosis species, *Escherichia coli*, Group A Streptococcus, Group B streptococcus, *Streptococcus pneumoniae, Helicobacter pylori, Francisella tularensis, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsii, Rickettsia akari, Rickettsia prowazekii, Rickettsia canada*, and *Coxiella burnetti*. Examples of yeast and other fungi that may be detected according to the invention include, but are not limited to, Aspergillus species (e.g. *Aspergillus niger*), *Mucor pusillus, Rhizopus nigricans*, Candida species (e.g. *Candida albicans, Candida dubliniensis, C. parapsilosis, C. tropicalis*, and *C. pseudotropicalis*), *Torulopsis glabrata, Blastomyces dermatitidis, Coccidioides immitis, Histoplasma capsulatum, Cryptococcus neoformans*, and *Sporothrix schenckii.*

Methods and kits of the invention may be used to detect and/or quantitate infectious agents associated with diseases, including, but not limited to, cutaneous anthrax, inhalation anthrax, gastrointestinal anthrax, nosocomical Group A streptococcal infections, Group B streptococcal disease, meningococcal disease, blastomycocis, streptococcus pneumonia, botulism, Brainerd Diarrhea, brucellosis, pneumonic plague, candidiasis (including oropharyngeal, invasive, and genital), drug-resistant *Streptococcus pneumoniae* disease, *E. coli* infections, Glanders, Hansen's disease (Leprosy), cholera, tularemia, histoplasmosis, legionellosis, leptospirosis, listeriosis, meliodosis, mycobacterium avium complex, mycoplasma pneumonia, tuberculosis, peptic ulcer disease, nocardiosis, chlamydia pneumonia, psittacosis, salmonellosis, shigellosis, sporotrichosis, strep throat, toxic shock syndrome, trachoma, traveler's diarrhea, typhoid fever, ulcer disease, and waterborne disease.

As those of ordinary skill in the art readily appreciate, the sample can be from any source. According to the present invention, the sample is typically an unknown substance, such as a powder or liquid, for example. Samples may be found outdoors or indoors. In one embodiment, a sample is an unknown powder found in or on an envelope, package, or other item of mail. In another embodiment, the sample is a bodily fluid such as blood, urine, spinal fluid, or other similar fluids. Alternatively, the sample is a fermentation medium such as from a biological reactor or food fermentation process such as brewing. The sample may also be food products such as milk, yogurt, cheese, meats, beverages and other foods. Other sources for samples include water, small amounts of solids, or liquid growth medium.

In one embodiment, viable cells in a sample are detected or quantified by comparing the fluorescence produced by the sample to the fluorescence produced by a control substance. Useful control substances are substances that do not contain live cells, including common powders such as, but not limited to, sugar, salt, baking soda, and powder coffee creamer. Fluorescence produced by the sample that is significantly greater than the fluorescence produced by the control substance indicates the presence of live cells in the sample. Significant differences should be at least two-fold and preferably 10-fold or greater.

Alternatively, or in addition, viable cells, and a viable viral and/or non-viral infectious agent, in a sample are detected by comparing the fluorescence produced by the sample to the fluorescence produced by a positive control substance. In some embodiments a means for enriching viable cells from viable viral or non-viral biowarfare agent is contemplated. A positive control substance may comprise any cell or molecule capable of binding the fluorescent dye to produce a measurable change in fluorescence. Suitable positive control substances may include, for example, DNA, bacteria, and yeast.

In another embodiment, viable cells in a sample are detected by comparing the fluorescence produced by the sample to standard measurements. Standards generally provide typical fluorescence measurements associated with different numbers and/or types of cells or DNA, for example. Standards, including those produced by control substances, may be determined in advance of testing of a sample in the field, or they may be prepared at approximately the same time or after testing a sample. Standard measurements may also be provided by a manufacturer or test laboratory.

The present invention requires that fluorescent dyes be actively internalized by viable cells in a sample and bind to their target cellular components. In addition, the invention requires that upon binding, the fluorescence properties of the dyes be altered to a measurable degree. The term "actively internalized" refers to fluorescent dyes that penetrate predominantly viable cells through a process other than passive diffusion across cell membranes. It includes, but is not limited to, internalization of fluorescent dyes through receptors on cell surfaces or through channels in cell membranes. As used herein, the term "actively internalized" may be interchangeably referred to as "internalized predominantly."

The target cellular components to which fluorescent dyes bind may be nucleic acids, actin, tubulin, nucleotide-binding proteins, ion-transport proteins, mitochondria, cytoplasmic components, and membrane components. Fluorescent dyes that fluoresce when metabolized by the cells in a sample, such as dequalinium aceteate, fluorescein diacetate, or other similar compounds, are also included in the invention.

Examples of fluorescent dyes that bind nucleic acids and suitable for the present invention include, but are not limited to, acridine orange (U.S. Pat. No. 4,190,328), calcein-AM (U.S. Pat. No. 5,314,805), DAPI, Hoechst 33342, Hoechst 33258, PicoGreen™, SYTO® 16, SYBR® Green I, Texas Red®, Redmond Red™, Bodipy® Dyes, Oregon Green™, ethidium bromide, propidium iodide, and the like. When such fluorescent dyes used to quantify viable cells in a sample, it is preferable there are no more than small differences in the nucleic acid content among the individual cells in the sample. The quantification method works accurately for samples containing predominantly a single species of bacteria or other specific cell types under normal growth conditions, such as in cheese starter cultures. However, variation in DNA content of microbes in axenic or microbial consortia cultures affects quantitative measurements less than the variation affects standard and other methods.

The present invention's detection and quantitative accuracy may also be affected by such factors as effective penetration of viable cells by the dye (which can be readily calculated for any dye), a low level of background fluorescence relative to the amount of fluorescence of dye bound specifically to DNA or other cellular components, low levels of exogenous DNA in the sample, and so on.

PicoGreen™ and SYTO® 16 are dyes particularly useful to the present invention and commercially available from Molecular Probes, Eugene, Oreg. PicoGreen™ is a cyanine dye with high molar absorptivity and very low intrinsic fluorescence. PicoGreen™ is specific for double strand DNA and produces large fluorescence enhancements (over 1000-fold) upon binding to DNA. Haugland, Richard P., *Handbook of Fluorescent Probes and Research Chemicals*, Molecular Probes, Eugene, Oreg., (1996). However, until the present invention it was not known to be taken up predominantly by viable cells. SYTO® 16 is a cell-permeant nucleic acid stain capable of staining most live and permeabilized bacteria, as well as eukaryotic cells. In addition, SYTO® 16 has proven particularly useful for detecting and/or otherwise distinguishing live from dead cells. Haugland, Richard P., supra.

Dyes are typically prepared by dissolving the dye in an aqueous solvent such as water, a buffer solution, or a water-miscible organic solvent such as dimethylsulfoxide (DMSO), dimethylformamide (DMF), methanol or ethanol. In certain embodiments, it is dissolved at a concentration of greater than about 100-times that used for staining samples. Preferably, the staining solution imposes no or minimal perturbation of cell morphology or physiology.

Before contacting fluorescent dyes, the sample or a fraction of the sample may first be rinsed in a buffer solution and centrifuged, filtered, or otherwise concentrated. The initial rinse solutions can be made in aqueous or other polar or semi polar solvents containing various salts between 0.05M and 1.0 M with a final pH of between 3.5 and 11.0 at temperatures between −20 degrees C. and 80 degrees C. The solutions may also contain reagents that maximize integrity of viable cells while releasing non-cellular materials into the solutions. Such reagents may include, by way of example but not in limitation, phosphates, neutral, anionic and cationic detergent (e.g., Tween® NP and Triton® series detergents, SDS, and cetyl-trimethyl ammonium BR, chaotropic salts (e.g., bile salts), organic acids (e.g. citrate), and lipids. In addition, when a fluorescent dye specific for DNA is used, the sample may be treated with a DNase to remove exogenous DNA before it is contacted with the dye.

As noted above, the fluorescent dyes need to be internalized by the cells to be detected and/or enumerated. In the preferred inventive method, an excess of the dye is used in order to saturate the cellular DNA in the sample. This can be determined by adding an amount known to be enough, or else by adding more and more until fluorescence ceases to increase.

In certain embodiments, multiple dyes may be used in order to detect more than one type of potential bioweapon. Means for multiband detections systems are well known in the art, for example, by way of example but not limitation, a multiwavelength fluorometer.

In certain embodiments, after contamination is washed from the cells, an agent that affects cell membrane properties may be used to treat the viable cells to speed the internalization process. Such agents include, but are not limited to, detergent-like compounds, surfactants, or other compounds that affect membrane polarity, fluidity, permeability, potential gradient or other membrane properties. Alternatively, DNA from the viable cells may be first extracted and then contacted with a fluorescent dye specific for DNA.

In the case that a sample is highly translucent, fluorescent dyes may be directly added to the sample and the relative fluorescence is then directly measured.

After being contacted with fluorescent dyes, the sample is excited by a light source capable of producing light at or near the wavelength of maximum absorption of the fluorescent complex, such a laser, an arc lamp, an ultraviolet or visible wavelength emission lamp. Any apparatus or device that can measure the total fluorescence of a sample can be used in this invention including flow cytometers. Typically, a standard fluorometer is used because of its relative low cost and field accessibility. The instrumentation for fluorescence detection may be designed for microscopic, surface, internal, solution, and non-suspension sample formats. The total fluorescence measured is then used to calculate the number of viable cells in the sample based on a predetermined value establishing a statistically relevant correlation between total fluorescence and the number of viable cells measured using any prior art method (e.g., standard plate count). The fluorescence may be measured at three or more intervals as the dye is entering the cells, so that the final fluorescence can be predicted in advance of saturation, thereby the time required to obtain a cell count is shortened. One of ordinary skill in the art would readily understand that any light source or measurement technique maybe used.

The invention also discloses a method of quantifying the ratio of viable cells to dead cells in a sample. In this embodiment, a sample containing both viable and dead cells is first saturated with an internalizing fluorescent dye. This dye does not need to be actively internalized by viable cells. It may diffuse into both viable and dead cells. After saturation, a second dye having emission wavelengths overlapping with those of the first dye is added to the mixture of the sample and the first dye. The second dye is capable of being internalized predominately by the viable cells in the sample. The internalization of the second dye quenches the fluorescence emitted by the first dye. The quenching effect of the second dye on the first dye can be used to calculate the ratio of viable cells to dead cells in the sample.

The present invention also discloses kits and apparatuses for detecting and quantifying viable cells. One such kit comprises a cell suspension solution, a fluorescent dye, and instruction for detecting the binding of the dye to cellular components of the viable cells and correlating the binding to cell number or colony forming units. The suspension solutions may be aqueous or other polar or semi-polar solvents containing various salts between 0.05M and 1.0 M with a final pH of between 3.5 and 11.0 at temperatures between −20 degrees C. and 80 degrees C. The solutions may also contain reagents that maximize integrity of viable cells while releasing non-cellular materials into the solutions as described above, a DNase, or an agent that affects cell membrane properties, such as a detergent. The fluorescent dye in the kit is capable of being actively internalized by the viable cells, binding to cellular components and altering its emission of fluorescence upon the binding to a measurable degree. The instruction contains necessary information of how to use the kit to detect or quantify viable cells in a sample, such as how to detect the fluorescence emitted from the dye and how to correlate the fluorescence measured with cell number or colony forming units.

In certain embodiments, kits may also include tools or devices useful for isolating a sample and/or placing a sample into a container or solution. For liquid samples, such tools or devices typically include pipettes and the like. For solid or powder samples, such tools or devices include scoops, swabs, cups, tubes, and the like, for example. A pipette may also be used for solid or powder samples. One of ordinary skill would recognize that a wide variety of tools may be used for this purpose.

In another aspect, a kit for quantifying live bacteria in a sample may include any one or combinations of the following: a cell suspension solution, means for placement of a sample into the solution, means for mixing the cell suspension solution with the sample, means for concentrating the cells, a fluorescent dye solution, means for mixing the dye solution with concentrated cells, and means for illuminating the resulting mixture with excitation light and measuring fluorescence emitted. The cell suspension solution may be the same as in the other kit described above. Any means for mixing solution with a sample known in the art (e.g., pipets, vortex) can be included in this kit. Any means for concentrating cells from solutions known in the art (e.g., centrifugation, filtration) may also be included in the kit. The fluorescent dye in the kit is capable of being actively internalized by the viable cells, binding to cellular components and altering its emission of fluorescence upon the binding to a measurable degree. Any means for illuminating a fluorescent solution with excitation light and measuring fluorescence emitted known in the art (e.g., flow cytometers, fluorometer) may be included in the kit.

Refinements of the above-described kits may include other dyes that bind uniquely to other cellular components of the sample, means for spectral and time-resolved analysis of the emitted fluorescent light, and means for separating the cell components to which the fluorescent dye binds from the sample before contacting with the fluorescent dye.

Depending on the properties of the fluorescent dye, the disclosed methods and kits may also be used in various assays other than viable cell identification and/or quantification. For instance, the use of fluorescent dyes that are capable of differentiating two kinds of cells (e.g. different bacteria or bacteria from yeast) enables the measurement of the ratio between the two kinds. The use of a fluorescent dye specific for a particular enzymatic activity may also be used to detect, identify, or quantify cells using the particular enzymatic activity. For example, fluorescein diacetate may be used to enumerate cells with active esterase. Such a fluorescent dye can be further used to enumerate cells in which a particular enzymatic activity is induced by certain chemicals (e.g., naphthalene and dequalinium acetate for the induction of esterase activity) or treatments (e.g., heat). In addition, fluorescent dyes that differentiate prokaryotes and eukaryotes based on their differences in cell membrane proteins, the presence or absence of certain organelles, and metabolism may be used to quantify prokaryotic cells, eukaryotic cells, or the ratio between the two types of cells. Furthermore, fluorescent dyes of which intensity is enhanced by contacting nucleated or enucleated cells in a sample that are known to be dead or not actively metabolizing in a sample may be used to enumerate such cells.

In other embodiments, fluorescent dyes that quench upon binding to specific cellular components after being predominantly internalized by viable cells may also be used to detect, identify, or quantify viable cells. In yet other embodiments, dyes or other substances that change the NMR signature of cells or any other bulk-detectable property of the cells may also be used for enumerating cells.

The present invention provides methods, kits, and apparatuses for simple dye associated identification or quantification that allows one to rapidly and inexpensively determine the presence and/or number of viable cells in a particular sample. One of ordinary skill in the art will readily appreciate that alternatives to the steps herein described for detecting or quantifying cells may be used and are encompassed herein. Accordingly, all alternatives will use a kit or method wherein a dye is utilized to stain cells and a detection method. Key aspects of the present invention include its rapid detection of viable cells and substantial cost savings as compared to previous systems.

All patents, patent applications and references cited herein are incorporated herein in their entirety. Accordingly, incorporated herein by reference are U.S. Pat. Nos. 5,437,980; 5,563,070; 5,582,984; 5,658,751; 5,436,134; Catt, S. L., Sakkas, D., Bizzaro, D., Bianchi, P. G., Maxwell, W. M. and Evans, G.; (1997) Molecular and Human Reproduction 3:821–825; Ferguson, L. R., and Denny, W. A.; (1995) Mutation Research 329:19–27; and Latt, S. A. and Wohlleb, J. D.; (1975) Chromosoma 52:297–316.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The following examples are offered by way of illustration, and not by way of limitation. All of the references, including patents, patent applications, and journal references are hereby incorporated by reference in their entirety.

EXAMPLES

Example I

Quantitation of Bacterial Cell Number

This example illustrates a method of enumerating live bacterial cells.

Solutions

Solution A. This is a wash/isolation solution that prepares the cells to take up the dye and permits removal of any interfering exogenous substances. All chemicals are reagent grade and can be obtained from common suppliers in the trade.

Ingredients and Preparation and Storage of Solution A (Ten Times Concentrate)

Ingredients:

| | |
|---|---|
| NaCl | 80.0 grams |
| KCl | 2.0 grams |
| $Na_2HPO_4$ | 14.4 grams |
| $KH_2PO_4$ | 2.4 grams |
| NaOH | sufficient to reach pH 7.4 |
| Pure water | sufficient for 1 liter |

Preparation:

The above chemicals are dissolved in 850 ml of pure water at room temperature. The pH is adjusted to 7.4 with 1M NaOH. The volume is adjusted to 1 liter with pure water. The solution is autoclaved and may be stored at room temperature for up to one year.

Ingredients Preparation and Storage of Stock Solution of Sodium Dodecyl Sulfate

Ingredients:

Sodium dodecyl sulfate (SDS) . . . 2.0 grams

Preparation:

Dissolve 2.0 grams of SDS in enough pure water to make a final volume of 100 ml.

Storage:

The solution may be stored for up to one year at room temperature.

Ingredients, Preparation and Storage of Working Solution A

Ingredients:

| | |
|---|---|
| Solution A (Ten Times Concentrate) | 100 ml |
| Stock Solution of SDS | 0.5 ml |
| Pure water | 900 ml |

Preparation:

Add the above solutions to a 1 liter container. Solution A is used in the invention.

Storage:

Solution A is autoclaved and then stored closed at room temperature.

Solution B. This solution contains a dye that stains viable cells. The formulation may allow unique stability and rapid uptake of the dye by the viable cells. All chemicals are reagent grade and can be obtained from common suppliers in the trade such as Sigma Chemical Co., St. Louis, Mo.

Ingredients and Preparation and Storage of Solution B.

Ingredients:

| | |
|---|---|
| Hoechst 33258 | 100 mg |
| Sterile pure water | 10 ml |
| Propylparaben | 0.1 ml (approximately-- this amount is not critical) |

Preparation of Solution B One Hundred Times Concentrate (an example using Hoechst 33258):

Solution B is made by dissolving Hoechst 33258 or similar dye in sterile pure water to a final concentration of 10 ug/ml. An antioxidant such as propyl gallate or propylparaben is added to increase shelf life of the solution.

Storage:

This solution is stored in the dark at 4 degrees C. It is stable for at least 6 months.

Dilution of Solution B

Ingredients:

| Solution B (One Hundred Times Concentrate) | 0.1 ml |
|---|---|
| Sterile, pure water | 9.9 ml |

Dilution:

Solution B (One Hundred Times Concentrate) is diluted 1/100 in sterile, pure water. For example, 100 ml of Solution B one Hundred Times Concentrate is dissolved into 9.90 ml of sterile, pure water for a final concentration of 0.1 mg/ml.

Reaction Solution Preparation for SYTO® 16 Dye and Spore Measurement

Remove frozen sample of 1 mM SYTO® 16 dye from the freezer and place on desktop to thaw (10–20 min).

Carefully pipet 1 ml of DMSO into a clean, autoclaved polypropylene tube.

Use a calibrated pipet to remove 50 µl of thawed SYTO® 16 dye from the sample vial, and add it to the tube containing 1 ml DMSO. This will yield a 50 µM final concentration for the working Reaction Solution.

Cap the polypropylene tube, and immediately wrap with aluminum foil, covering the sides and top.

Vortex the tube for a few seconds to ensure complete mixture of the chemicals.

Cell Prep Solution Preparation (TNE buffer)

*Recipe calls for: 10 mM Tris, 1 mM EDTA, 50 mM NaCl-titrate to pH 7.4

Measure out approximately 985 ml of deionized/distilled water in a large graduated cylinder and pour into a large Erlenmeyer flask. Set aside In a weigh boat, carefully weigh out 1.576 g of Trizma HCl. Add to flask.

Repeat measurement, weighing out 2.922 g of NaCl. Add to flask.

Measure out 282 mg of EDTA powder OR use 11.76 ml of prepared 0.085M EDTA solution. Add to flask.

Agitate flask to ensure that all chemicals mix together thoroughly.

Using NaOH and a Pasteur pipet, titrate cell prep solution to a pH of 7.4. If necessary, top off solution with deionized/distilled water to a final volume of 1000 ml.

Autoclave and sterile filter solution.

Sample Collection and Fluorescence Measurement

One particularly useful fluorometer is the GP320 handheld fluorometer by Turner Designs in Sunnyvale, Calif. Any fluorometer with filters appropriate for the dye used is useful. The wavelengths used for the detection of spores using SYTO® 16 in the Prime Alert™ method are:

475 nm excitation and 515 nm emission.

Calibrate the GP320 reader with the solid "B" calibration standard, making sure that the GP320 is in B mode. For calibration instructions, see page 8 of the Prime Alert Instruction Manual. To change the mode on the GP320, push the A/B button until "B" appears in the data screen.

Use the pre-filled Prime Alert dropper bottle to fill an empty test vial with 8 drops of Prime Alert cell prep solution. Set test vial aside.

Using the Prime Alert sampling device, collect one scoop of sample powder. Use the spatula to gently pack and level off the scoop, and to eliminate excess powder from the scoop edges and bottom.

Remove the screw-top lid and empty the scoop into the dropper bottle. To ensure that the entire sample has been ejected from the scoop, tap the scoop against the walls of the dropper bottle. If possible, avoid submerging the scoop in the Prime Alert cell prep solution.

Replace the dropper bottle screw-top lid, and tighten. With the cap secure on the end of the spout, vigorously shake the dropper bottle for several seconds. Remove the cap from the end of the spout and add 4 drops of the sample solution into the previously filled test vial.

Using the transfer pipet, draw the 50 µM Prime Alert Reaction Solution into the pipet, and then expel the full volume into the test vial containing the sample solution. Cap and shake the test vial, then place it in the GP320. Press READ.

Methods

The procedure given below discloses an example of a method for quantitating bacteria present in a liquid suspension using the invention.

1. Calibration and Blanking of the Fluorometer

A simple table-top fluorometer such as Turner Designs model 360 is used which is fitted with a set of filters, 365 nm excitation light wavelength and 460 nm emission light wavelength. A calibration solution of known fluorescence intensity is employed to calibrate the instrument to a reading of zero. A blank solution such as Solution A is used to set the instrument to a reading of zero. All procedures are carried out at room temperature.

Blanking Procedure:

a) place blank standard solution in reader (fluorometer) cuvette b) close lid of fluorometer and push "blank" on keypad c) adjust the fluorometer to read 5000 relative fluorescent units Calibration Procedure:

a) place unique "calibration solution" in cuvette b) close lid of fluorometer and push "calibration" on keypad c) adjust the fluorometer to read 5000 relative fluorescent units 2. Method for Counting Bacteria a) Add 200 microliters of Solution A to the cuvette containing bacterial cells.

b) Add a 5 microliter volume of bacterial cells to Solution A in the cuvette.

c) Centrifuge at 2000 g for 30 seconds.

d) Remove the supernatant solution by shaking or pipetting to remove it while retaining the cells.

e) Add 200 microliters of Solution A to the cuvette containing bacteria and vortex to suspend the cells.

f) Centrifuge at 2000 g for 30 seconds.

g) Remove the supernatant solution by shaking or pipetting, while retaining the cells.

h) Add 100 microliters of Solution B, vortex to suspend the cells and incubate for 10 min at room temperature.

i) Place cuvette in fluorometer, close the lid and record the relative fluorescence value.

j) Correlate the relative fluorescence reading with colony forming units/ml.

Data

Figure 1:
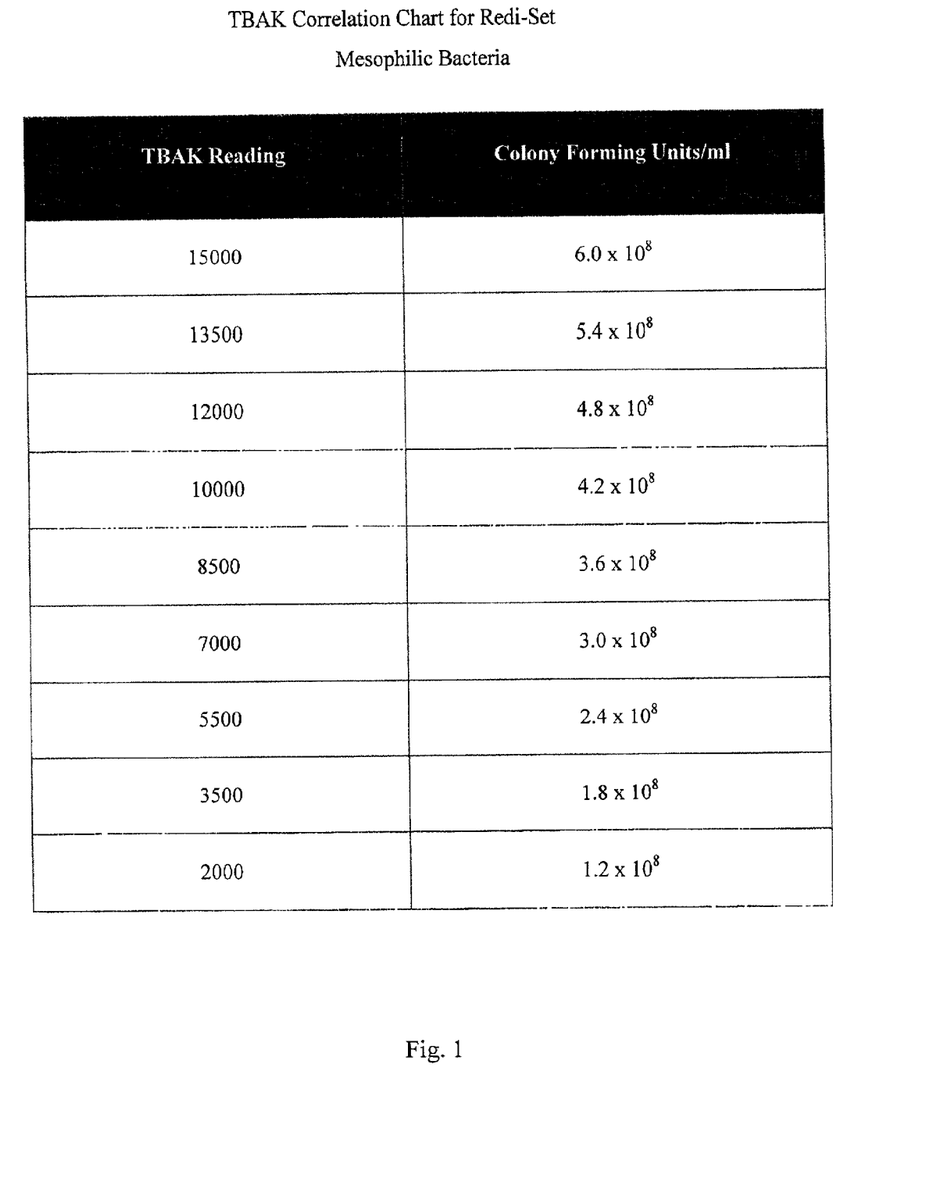
Figure 2:
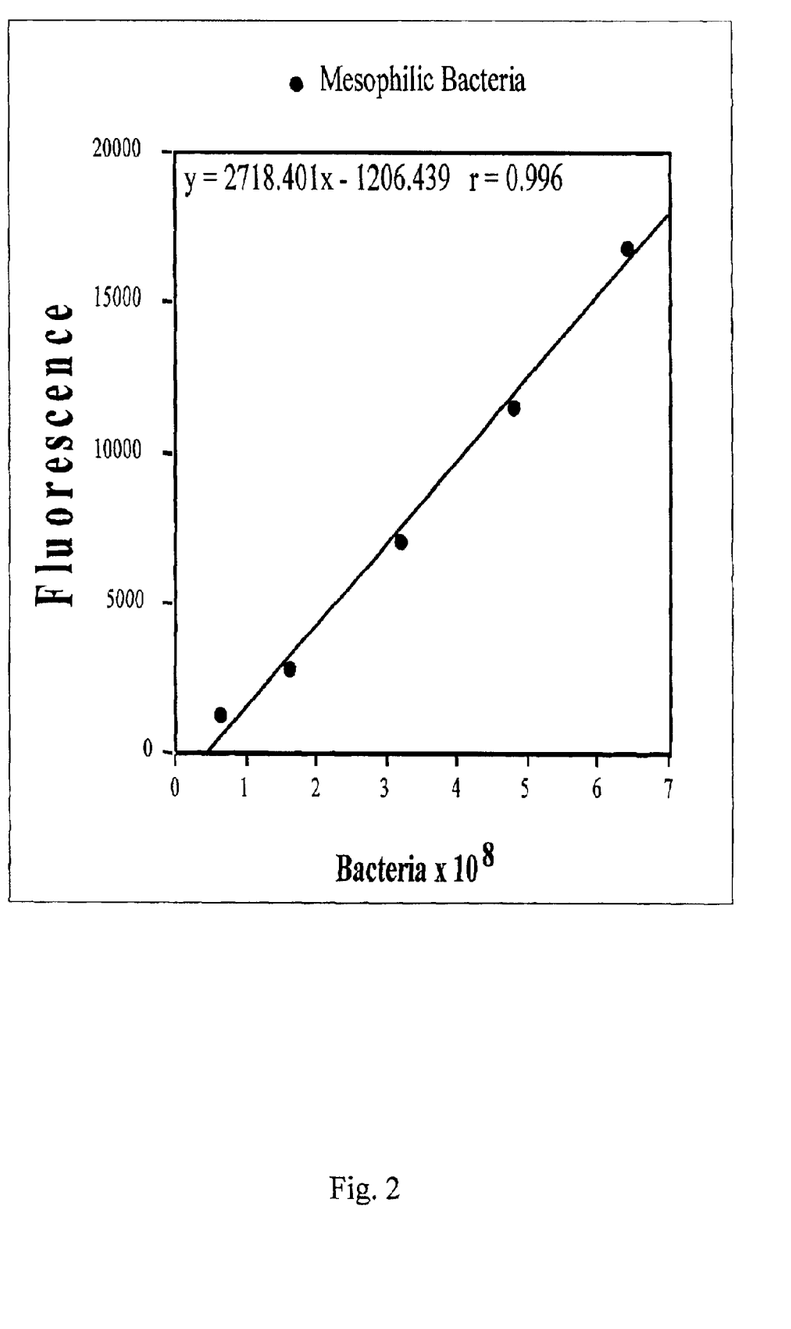
Figure 3:
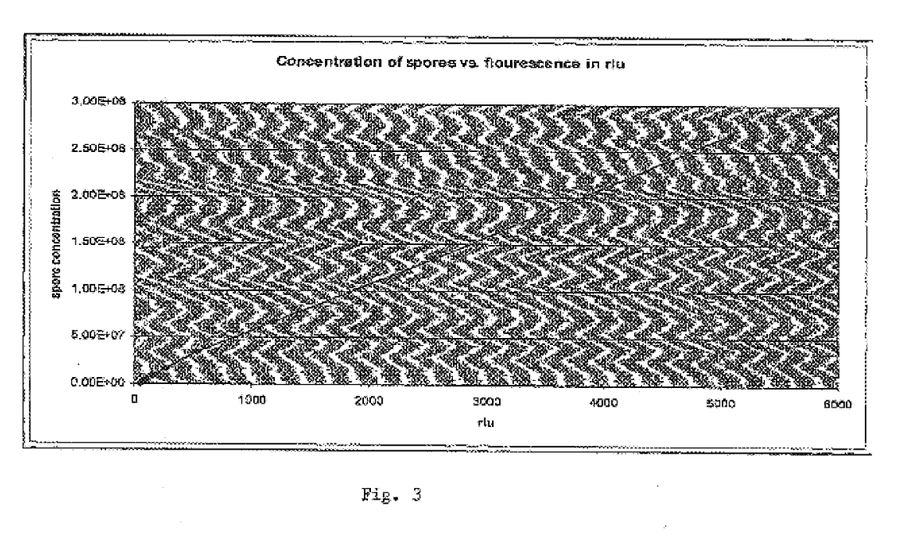
Figure 4:
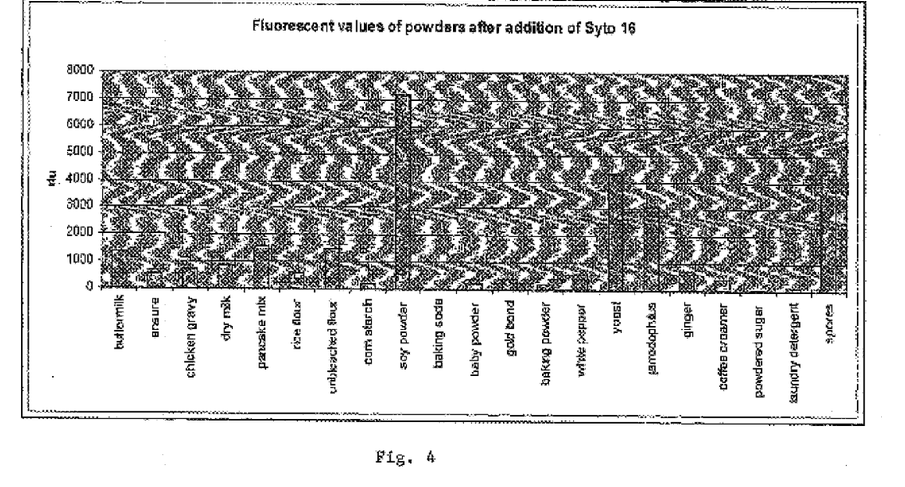

FIG. 2 is an example of a correlation of relative intensities of fluorescence emission (TBAK readings) to the standard plate counts (colony forming units/ml). FIG. 3 is another example of correlation of relative fluorescence readings with colony forming units/ml in a chart form. Both figures indicate that the intensity of the fluorescence emission is directly proportional to the cell numbers as measured by the standard plate count method.

What is claimed is:

1. A method for detecting the presence of viable cells in a sample, comprising:
   a) contacting a sample with a fluorescent dye that binds to target components of a viable cell, wherein said dye is internalized predominately by viable cells and has fluorescence properties that are measurably altered when bound to target components;
   b) detecting total fluorescence of said sample; and
   c) comparing the fluorescence detected in step (b) to the fluorescence produced by a control substance, thereby detecting viable cells, wherein the fluorescent dye is SYTO® 16.

2. A method for detecting the presence of viable cells in a sample, comprising:
   a) contacting a sample with a fluorescent dye that binds to target components of a viable cell, wherein said dye is internalized predominately by viable cells and has fluorescence properties that are measurably altered when bound to target components;
   b) detecting total fluorescence of said sample; and
   c) comparing the fluorescence detected in step (b) to the fluorescence produced by a control substance, thereby detecting viable cells, wherein the fluorescent dye binds to DNA of the cells, further comprising treating the sample with DNase before contacting the sample with the fluorescent dye.

3. A method for detecting the presence of viable cells in a sample, comprising:
   a) contacting a sample with a fluorescent dye that binds to target components of a viable cell, wherein said dye is internalized predominately by viable cells and has fluorescence properties that are measurably altered when bound to target components;
   b) detecting total fluorescence of said sample; and
   c) comparing the fluorescence detected in step (b) to the fluorescence produced by a control substance, thereby detecting viable cells, wherein the fluorescent dye is SYTO® 16, further comprising correlating the fluorescence detected in step (b) to the number of viable cells in the sample.

4. A method for detecting the presence of viable cells in a sample, comprising:
   a) contacting a sample with a fluorescent dye that binds to target components of a viable cell, wherein said dye is internalized predominately by viable cells and has fluorescence properties that are measurably altered when bound to target components;
   b) detecting total fluorescence of said sample; and
   c) comparing the fluorescence detected in step (b) to the fluorescence produced by a control substance, thereby detecting viable cells, wherein the fluorescent dye binds to DNA of the cells, further comprising treating the sample with DNase before contacting the sample with the fluorescent dye, further comprising correlating the fluorescence detected in step (b) to the number of viable cells in the sample.

5. The method of any one of claims 1, 2, 3, or 4 wherein the cells in the sample are selected from the group consisting of: bacteria, spores, yeast, DNA containing viruses, and fungi.

6. The method of claim 5 wherein the bacteria are selected from the group consisting of: *Bacillus anthracis, Bacillus cereus, Clostridium botulinum, Yersinia pestis, Yersinia enterocolitica, Francisella tularensis*, Brucella species, *Clostridium perfringens, Burkholderia mallei, Burkholderia pseudomallei*, Staphylococcus species, Tuberculosis species, *Escherichia coli*, Group A Streptococcus, Group B streptococcus, *Streptococcus pneumoniae, Helicobacter pylori, Francisella tularensis, Salmonella enteritidis, Mycoplasma hominis, Mycoplasma orale, Mycoplasma salivarium, Mycoplasma fermentans, Mycoplasma pneumoniae, Mycobacterium bovis, Mycobacterium tuberculosis, Mycobacterium avium, Mycobacterium leprae, Rickettsia rickettsii, Rickettsia akari, Rickettsia prowazekii, Rickettsia canada, Bacillus subtilis, Bacillus subtilus niger, Bacillus thuringiensis* and *Coxiella burnetti*.

7. The method of claim 5 wherein the cells are *Bacillus anthracis*.

8. The method of claim 5 wherein the spores are *Bacillus anthracis, Bacillus cereus, Bacillus subtilis, Bacillus subtilus niger*, and *Bacillus thuringiensis*.

9. The method of claim 5 wherein the yeast are selected from the group consisting of: Aspergillus varieties, *Mucor pusillus, Rhizopus nigricans, Candida albicans, C. parapsilosis, C. tropicalis, C. pseudotropicalis, Torulopsis glabrata, Aspergillus niger*, and *Candida dubliniensis*.

10. The method of claim 5 wherein the fungus is selected from the group consisting of: *Blastomyces dermatitidis, Coccidioides immitis, Histoplasma capsulatum*, Aspergillus species, Candida species, *Cryptococcus neoformans*, and *Sporothrix schenckii*.

11. The method of any one of claims 2 or 4 wherein the fluorescent dye is selected from the group consisting of: acridine orange, Hoechst 33258, PicoGreen™, SYTO® 16, SYBR® Green I, Texas Red®, Redmond Red™, Bodipy® Dyes, and Oregon Green™.

12. The method of any one of claims 1, 2, 3, or 4 further comprising treating the sample with an agent that affects a cell membrane property of the cells.

13. The method of claim 12 wherein the agent is a detergent.

14. A kit for detecting viable cells in a sample, comprising a cell suspension solution, a fluorescent dye that can be internalized predominantly by viable cells, and instructions for detecting dye binding to cellular components of viable cells.

15. The kit of claim 14 wherein the cell suspension solution comprises a DNase.

16. The kit of claim 14 wherein the cell suspension solution comprises an agent that affects a cell membrane property of the viable cells.

17. The kit of claim 16 wherein the agent is a detergent.

18. The kit of claim 16 wherein the fluorescent dye is selected from the group consisting of: acridine orange, Hoechst 33258, PicoGreen™, SYTO® 16, SYBR® Green I, Texas Red®, Redmond Red™, Bodipy® Dyes, and Oregon Green™.

19. The kit of claim 18 wherein the fluorescent dye is SYTO® 16.

20. A kit for detecting or quantifying viable cells, comprising: instructions for detecting or quantifying viable cells, a first container containing a first solution, means for placement of a sample containing an unknown number of viable cells into a solution containing a fluorescent dye that can be internalized predominately by the viable cells and binds selectively to double-stranded DNA or other specific cellular components, whereupon its fluorescence is altered to a measurable degree, and means for illuminating the mixture of first solution with said sample with excitation light and measuring fluorescence emitted by said mixture, thereby detecting the presence of viable cells in said sample.

21. A kit for detecting or quantifying viable cells, comprising: instructions for detecting or quantifying viable cells, a first container containing a first solution, means for placement of a sample containing an unknown number of viable cells into a first solution, means for concentrating the solids and cells from the mixture of said first solution with said sample and retaining said solids from the remainder of said mixture, a second solution containing a fluorescent dye that can be internalized predominately by the viable cells and binds selectively to double-stranded DNA or other specific cellular components, whereupon its fluorescence is altered to a measurable degree, means for mixing said second solution with said solids to form a second mixture, and means for illuminating the mixture of said second solution with said solids with excitation light and measuring fluorescence emitted by said mixture, thereby detecting viable cells in said sample.

22. The kit of claim 20 or 21 wherein the fluorescent dye in said solution is SYTO® 16.

* * * * *